United States Patent [19]

Wagner

[11] 4,178,510
[45] Dec. 11, 1979

[54] DEVICE FOR MEASURING THE SPATIAL DISTRIBUTION OF RADIATION ABSORPTION IN A SLICE OF A BODY

[75] Inventor: Wolfgang Wagner, Norderstedt, Fed. Rep. of Germany

[73] Assignee: U.S. Philips Corporation, New York, N.Y.

[21] Appl. No.: 807,039

[22] Filed: Jun. 16, 1977

[30] Foreign Application Priority Data

Jun. 22, 1976 [DE] Fed. Rep. of Germany ....... 2627885

[51] Int. Cl.² .............................................. A61B 6/02
[52] U.S. Cl. .................................. 250/445 T; 250/360
[58] Field of Search ............................ 250/445 T, 360

[56] References Cited

U.S. PATENT DOCUMENTS 4,071,760  1/1978  LeMay ............................ 250/445 T

Primary Examiner—Alfred E. Smith
Assistant Examiner—T. N. Grigsby
Attorney, Agent, or Firm—Thomas A. Briody; Edward J. Connors, Jr.; Jack E. Haken

[57] ABSTRACT

In third-generation transversal tomography scanners, where the total body slice to be examined is irradiated by a flat, fan-shaped radiation beam, the probability that a detector which measures part of the radiation in the radiation beam becomes defective is very high. This failure causes artefacts in the reconstruction of the absorption distribution of the slice of the body, said artefacts having an adverse effect on the evaluation of the image by the radiologist. The invention ensures that a defective detector is identified (for example, by comparison of the measuring values supplied by each detector with the measuring values of adjacent detectors), the measuring value of a detector which has been identified as being defective being replaced by a correction value which can be formed by interpolation of measuring values obtained along neighboring paths.

35 Claims, 6 Drawing Figures

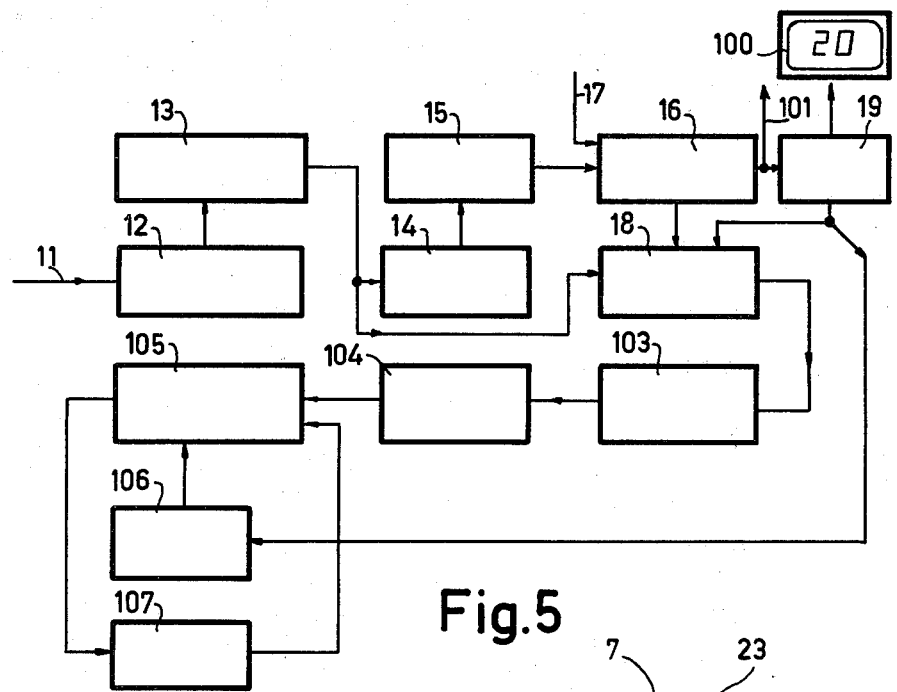
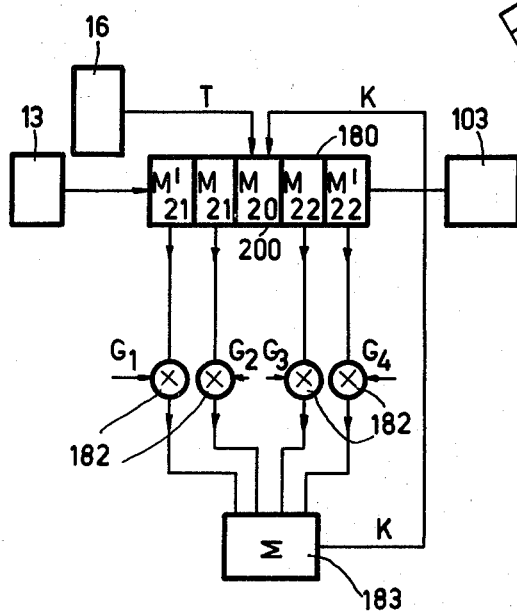
Fig.6
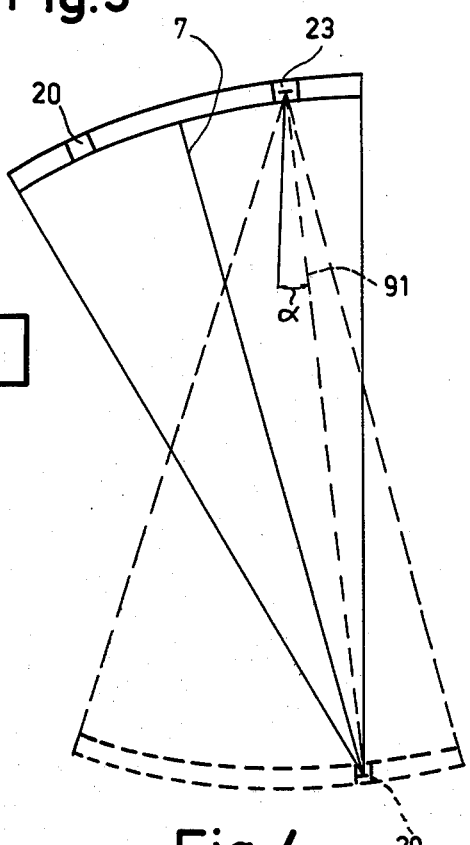
Fig.4
Fig.5

DEVICE FOR MEASURING THE SPATIAL DISTRIBUTION OF RADIATION ABSORPTION IN A SLICE OF A BODY

BACKGROUND OF THE INVENTION

1. Field of the Invention

The invention relates to a device for measuring the spatial distribution of radiation absorption in a slice of a body, said device comprising a radiator (for example, an X-ray tube) for generating a fan-shaped radiation beam for irradiating the body, a row of adjacently arranged radiation detectors for determining measuring values concerning the radiation emerging from the body, the measurements being performed in a number of different angular positions of the radiator/detector system with respect to the body, the direction of the radiation beam extending in the slice of the body, and also comprising a reconstruction device for determining the absorption distribution in the slide on the basis of the measuring values obtained. A device of this kind is known from U.S. Pat. No. 3,937,963.

2. Description of the Prior Art

The advantage of a device of this kind over a device comprising only a single detector such as described, for example, in British Patent specification No. 1,283,915, consists in that the measurement can be performed faster, because a large number of measuring values can be simultaneously obtained and because for the measurement of the radiation absorption in the slice it is only necessary to rotate the radiator/detector system about an axis which extends perpendicularly to the slice, preferably through the body to be examined. There is a drawback, however, in that the probability of at least one of the many detectors required being defective is no longer negligibly small. If a detector is defective, the measurement of the absorption on the basis of the measuring values determined by the detectors is disturbed.

A defective detector is not to be understood herein a detector which produces a change of a measuring value due to temperature influences or aging, in which case changes in the order of a few percent of the measuring value occur. Such a fluctuation in the measuring value usually influences all detectors to the same extent. For the correction of such fluctuations, devices are already known (German Offenlegungsschrift No. 25 13 137) which are based on the assumption, however, that the relative fluctuation of a measuring value during the measurement is small. A defective detector is to be understood to mean herein the complete breakdown of a detector or an amplifier associated with this detector, or a sudden and irregular fluctuation of the measuring value thereof at constant X-radiation. Phenomena of this kind can occur, for example, due to partial or complete damaging of a detector by excessive X-radiation, due to mechanical damage or due to incorrect contact connections in the amplifiers associated with the detector.

It has been found that a defect in one or more detectors gives rise to circular or beam-like interference patterns during the reconstruction of the absorption distribution, said patterns making the interpretation of the absorption values thus obtained difficult or even impossible.

SUMMARY OF THE INVENTION

The invention has for its object to provide a device of the described kind in which the disturbances caused by a defective detector are substantially eliminated during the reconstruction of the absorption distribution in the slice. To this end, the examining device in accordance with the invention is characterized in that the device comprises a testing device for identifying defective detectors, and also an interpolation unit for replacement of measuring values of a detector which has been identified as being defective by correction values, formed by interpolation of measuring values measured along paths adjacent the paths along which the measuring values have been measured by the defective detector.

A defective detector can then be unambiguously identified, for example, when it supplies a constant measuring value, notably the value zero, regardless of the position occupied by the radiator/detector system, while both neighbouring detectors supply measuring values other than zero which vary when the angular position changes. Physical effects can also be utilized for identifying defective detectors, for example, the variation of the resistance characteristic in the case of a defective semiconductor detector.

Whether or not the reduction of the disturbances in the reconstruction of the absorption distribution by the replacement of the measuring values of a defective detector by the correction values obtained by interpolation alone is sufficient, is dependent on the one hand on the absorption distribution in the slice of the body and on the other hand also on the nature of the reconstruction method. According to the reconstruction method which is known from U.S. Pat. No. 3,936,636, where the measuring values are subjected to a convolution process (where a convoluted value is obtained from a measuring value and the correctly weighted sum of the measuring values along parallel, neighbouring paths), the errors which remain in spite of interpolation are intensified. This error intensification is a property of the convolution process and can only be slightly influenced.

A further embodiment of the device which is suitable for use in devices where the radiator/detector system is rotated through an angle of 360° or more during the measurement and which comprises means for performing a convolution process with the measuring values and correction values obtained, is characterized in that the device comprises an arithmetic device for substituting each correction value by a value which is formed from one or more measuring values measured either along a path directly adjacent the path associated with the correction value or by a detector which is symmetrically arranged with respect to the defective detector, relative to the symmetry line of the detector row, or by the neighbouring detectors thereof. Thus, any residual errors in the reconstruction are also substantially eliminated.

One embodiment of the device in accordance with the invention will be described in detail hereinafter with reference to the drawing.

BRIEF DESCRIPTION OF THE DRAWINGS

FIG. 4 shows the position of the radiator/detector system, the measuring value being obtained along a same path as shown in FIG. 1 by measurement in the opposite direction, FIG. 5 shows a block diagram of a part of the device in accordance with the invention, and FIG. 6 is a more detailed view of a part of the block diagram shown in FIG. 5.

BRIEF DESCRIPTION OF THE PREFERRED EMBODIMENT

Figure 1:
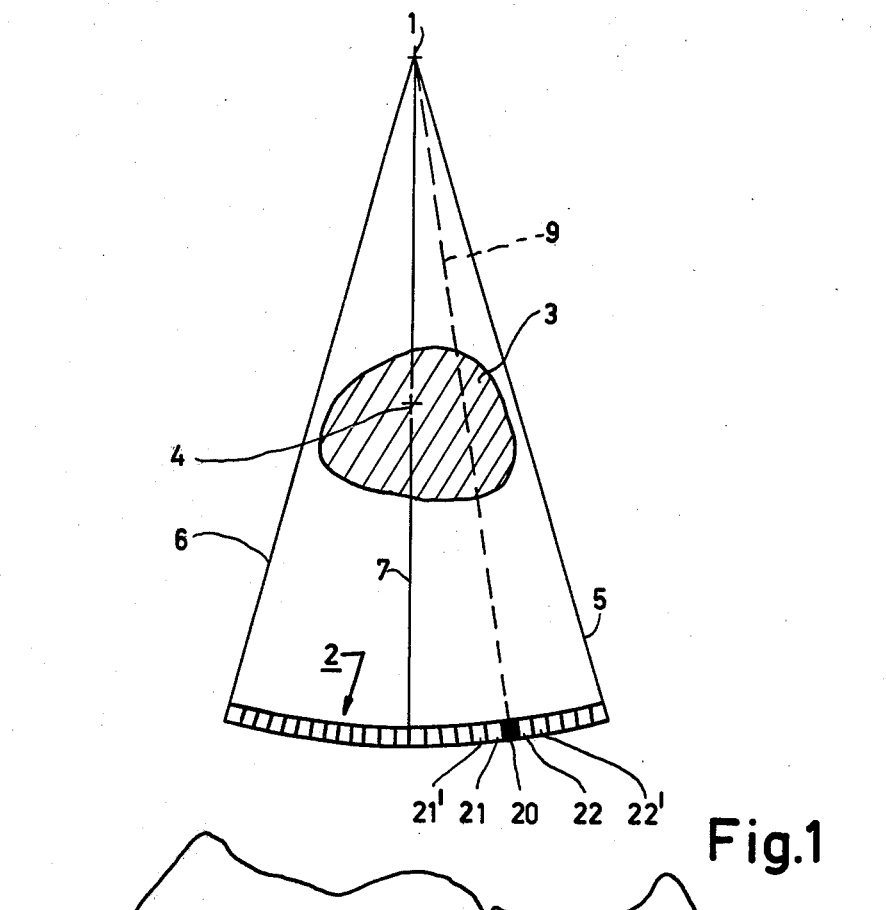
FIG. 1 shows the geometrical configuration of the radiator, the body and the row of detectors of a device in accordance with the invention.

The reference numeral 1 in FIG. 1 denotes an X-ray radiator, the fan-shaped beam of which is bounded by rays 5 and 6. The radiation passes through the sice 3 of a body to be examined and is measured by a row of detectors 2 which is arranged behind the body. The left half and the right half of the detector row 2 are symmetrically constructed with respect to the symmetry line 7. During a measurement, the radiator/detector system is rotated around the center of rotation 4 and the radiation emitted by the radiator 1 is measured in a large number of different positions. Correctly operating detectors 21 and 22 adjoin a defective detector 20 which measures the absorption of the radiation by the body along the path 9 in the position of the radiator/detector system shown.

The solution proposed in accordance with the invention is based on the recognition of the fact that the radiation absorption by the body along neighbouring paths deviates only comparatively little, so that large errors cannot occur when the measuring values of the defective detector 20 are replaced by correction values. The correction values are formed by interpolation from measuring values measured along neighbouring paths. For this purpose, use is made of the measuring values measured in the same position of the radiator/detector system by the neighbouring detectors 21 and 22 (and possibly also the neighbouring detectors 21' and 22'); these measuring values determine the radiation absorption along paths which do not extend exactly parallel to each other. However, use can alternatively be made of measuring values which represent the absorption along directly adjoining, but accurately parallel extending paths (the method of obtaining these measuring values is disclosed in German Offenlegungsschrift 25 17 440. Linear interpolation from the measuring values along both directly adjoining radiation paths generally is not accurate enough. The correction value will be more likely formed by at least two, preferably three, measuring values along the two or three, respectively, paths situated on both sides.

Figure 2:
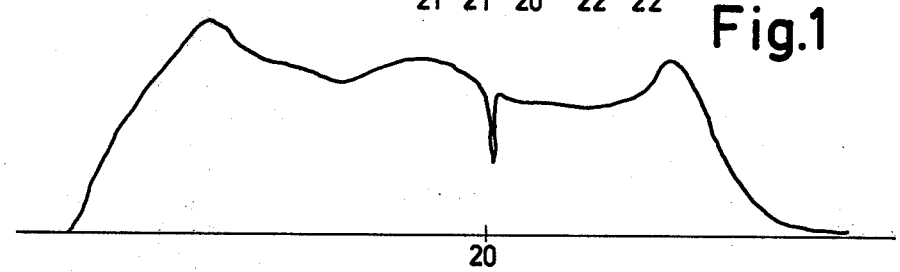
FIG. 2 shows the variation of the measuring values of each detector as a function of the adjacently situated detectors.
Figure 3:
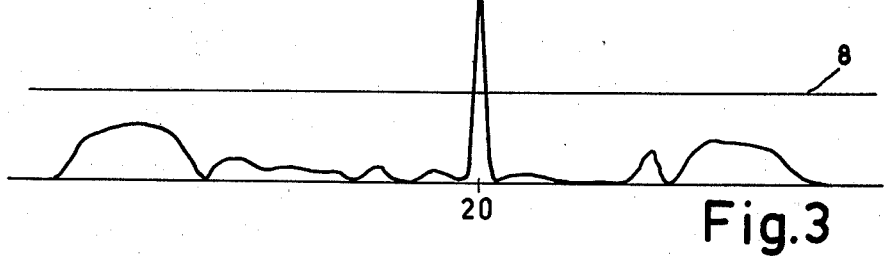
FIG. 3 shows the variation of the differences of each sum of the measuring values of each detector of FIG. 2 as a function of the adjacently situated detectors.

FIG. 2 shows for each detector the sum of the measuring values recorded thereby in the various rotary positions as a function of the adjacently situated detectors. It will be seen that the sum values of the adjacently situated detectors deviate only comparatively little from each other, a peak-like irregularity occurring only in the region of the detector 20. This effect is utilized for identifying a defective detector. This is because if the value of the difference between the sum value of a detector and that of a neighbouring detector (or both neighbouring detectors) is determined separately for each detector, the variation of the value of the difference shown in FIG. 3 is obtained, said difference being very significant at the area of the detector 20 with respect to the other detectors. The difference value associated with the neighbouring detector is also substantially larger than the other difference values, because the sum value of the defective detector is taken into account in this difference value. The two difference values which deviate substantially from the average value, however, are adjacently situated and the defective detector 20 or the position thereof in the detector row can be readily determined on the basis thereof. To this end, a threshold value 8 is introduced which may be a constant value for all measurements, but which may alternatively be, for example, a multiple of the mean difference value. A detector whose associated difference value exceeds this threshold value, can thus be readily identified as being defective.

A further possibility of identifying defective detectors exists in devices where the radiator/detector system is rotated through an angle of 360° or more during the measurement; this offers certain advantages which will not be described herein. Each measuring value measured by a given detector in a given rotary position is then associated with a second, substantially equally large measuring value which has been measured by a detector situated symmetrically with respect to the defective detector, relative to the symmetry line, that is, in a position of the radiator/detector system which differs from the first position by a rotation of $180° + 2\alpha$, $\alpha$ being the angle at which the defective detector is "seen" by the radiator, relatively with respect to the symmetry line 7 (this value may have a positive or negative value, depending on whether the defective detector is situated in the front half or in the rear half of the detector row with respect to the direction of rotation). This is illustrated with reference to FIG. 4, in which the radiator/detector system is shown in a position in which the detector 23, being symmetrically arranged with respect to the defective detector 20, relative to the symmetry line 7, measures the radiation along a path 91 which has the same position as the path 9 of FIG. 1, but in the opposite direction.

Thus, two measuring values can be compared. In the case of deviations of the pairs of measuring values, the incorrect functioning of one of the two detectors can be determined. However, if all measuring values are compared in this manner, a substantially larger quantity of arithmetical operations and more time is required than for the method of identifying a defective detector described with reference to the FIGS. 2 and 3.

A third possibility of identifying defective detectors exists in devices which comprise means for the correction of drift phenomena of detectors, caused by temperature fluctuations and aging. To this end, the radiator/detector system of a known device is rotated out of the measuring region into an other region in which a body having a known X-ray absorption is provided. The measuring values measured on this absorption body are compared with the known, actual values. on the basis of which a correction quantity can be derived for each detector. If one of the detectors is defective, it is to be expected that the correction quantity thereof deviates substantially from its correction quantity determined during a previous measurement and also from the correction quantity of other detectors. If deviations of this kind occur in several successive correction measurements, it can be deduced that the detector is defective.

The positions of the detectors identified as being defective in accordance with one of the three described methods are effectively stored so as to be taken into account for the subsequent measurements. Preferably, the position (positions) of the defective detector (detectors) is (are) displayed on a display apparatus in order to inform the testing personnel.

FIG. 5 diagrammatically shows the block diagram for the reconstruction of the absorption distribution on the basis of measuring values produced in part by defective detectors. The measuring values determined by means of the radiator/detector system are applied in known manner, by the lines 11 (the drawing shows only one line for the sake of simplicity), to a logarithmic unit 12 which determines the natural logarithm of the measuring values after subtraction of a reference value. The logarithmic measuring values are temporarily stored in a memory 13 which may be formed, for example, by a disc memory or a semiconductor memory. Because the overall measuring time amounts to only a few seconds in a device of the described kind, it is not important that the further processing of the measuring values takes place only after completion of the measurement.

An arithmetic unit 14 calculates the absolute differences between all neighbouring measuring values in the first rotary position, these differences being stored separately for each detector position in the memory 15. The differences for the next rotary position subsequently calculated in 14 are added to the differences already stored in the memory 15, again separately for each detector position. Thus, the mean values of the differences for each detector position are calculated (as has already been described with reference to the FIGS. 2 and 3, it is of course also possible to add the measuring values of each detector first and to subsequently form the differences of the sum values thus obtained).

Subsequently, the difference values obtained are compared in a comparison unit 16 with a predetermined threshold value (8; FIG. 3) by the line 17. This predetermined threshold value can be calculated by further averaging of all difference values stored in the memory 15, or it may be externally put in because it does not substantially change from one measurement to the next measurement. If no detector is defective, none of the difference values formed will exceed the threshold value. If a detector is defective, the associated difference value and the difference value associated with a neighbouring detector will exceed (for the reasons described with reference to FIG. 3) the threshold value. However, one of these two detectors can always be unambiguously identified as being defective; for example, if the measuring value of the right-hand neighbouring detector is used for the formation of the difference in the arithmetic unit 14, the left one of the two detectors is defective (and vice versa).

The position thus obtained of a detector in a detector row is applied on the one hand, by a line 101, to a process computer (not shown), said computer comparing the newly obtained position with the positions of defective detectors already obtained during previous measurements and stored in the memory 19. If the newly obtained positions correspond to the positions previously stored in memory 19, an even stronger indication exists as regards the defective condition of the relevant detector. However, if the newly obtained positions often do not correspond to the positions already stored in 19, there is an indication that the preset threshold value is too low. Thus, the preset threshold value can be optimized by a continuous check of the positions obtained. Moreover, the newly obtained positions are stored in the memory 19 for later use. The memory 19 has connected to it an indicator 100 which indicates the position of the defective detectors to the user. The positions of the detectors identified as being defective are applied to the interpolation unit 18, which replaces the associated measuring value by interpolation of the measuring value of neighboring detectors.

FIG. 6 shows a feasible embodiment of the interpolation unit 18. The interpolation unit comprises a shift register 180, having five memory cells in which the measuring values of all detectors, obtained in a given position of the radiator detector system, are put in in series and are shifted from left to right. The outputs of the five memory cells of this shift register, with the exception of the third memory cell 200, are connected to multipliers 182 which multiply the contents of each of the memory cells by a predetermined weighting factor $G_1$, $G_2$, $G_3$ and $G_4$, respectively. The products thus formed are summed in a summing unit 183, the result being stored in the last memory cell but two (200) if a take-over signal T which can be derived from the comparison device 16 is present at the cell 200.

When the detector whose measuring value is stored in the memory cell 200 is not defective, the gates 181 and 184 are blocked by the comparison device 16 or the memory 19 for the defective detectors. However, if the memory 200 cell contains a measuring value originating from a defective detector, the gates 181 and 184 are conductive, and a correction value K appears on the output of the summing stage 183, in which case $$K = G_1 M_{21}' + G_2 M_{21} + G_3 M_{22} + G_4 M_{22}'.$$

Therein, $M_{21}$ and $M_{21}'$ and $M_{22}$ and $M_{22}'$ are the measuring values of the two detectors which are adjacent the defective detector and $G_1 \ldots G_4$ being interpolation factors. Obviously, other interpolation formulas can also be used. The correction value K thus formed is stored, through the gate 184 which is then conductive, in the memory cell 200 instead of the measuring value $M_{20}$ of the defective detector. Subsequently, the measuring values stored in the shift register are shifted one position to the right, the measuring value present in the last memory cell (which may possibly be a correction value K) being input into the unit 103 (see FIG. 5) for further processing. The described formation of the correction value is repeated each time when the memory cell 200 contains a measuring value originating from a defective detector.

Thus, the measuring values of all detectors or the calculated correction values for all positions of the radiator/detector system are put into the unit 103. The measuring values are sorted in this unit 103 so that groups of measuring values are formed, each group containing only measuring values which represent the absorption along parallel paths. This processing phase, known from the described devices, will not be elaborated herein. This processing phase is generally a condition for the convolution operation taking place in the unit 104 whereby each measuring value or correction value is converted into a value which is not only dependent of the measuring value itself, but also of the measuring values or correction values along neighbouring parallel paths. The measuring values thus converted are stored in the memory 105.

As has already been stated, the convolution process has the property that errors which arise due to the fact that the correction values do not exactly correspond to the measuring values which would have been determined in the case of non-defective detectors, are substantially intensified. In order to avoid the errors thus produced, an address calculating machine 106 is connected to an interpolation unit 107. The positions of the defective detectors are applied in advance to the address calculating machine 106 by the memory 19 for the defective detectors. On the basis thereof, the address calculating machine 106 calculates the addresses at which the measuring value is stored which has been converted by the convolution process and which has been measured along the path, such as each time the measuring value of a defective detector, but in the reverse direction (see FIG. 4), so that, for example, for the correction value calculated along the path 9 by the detector 20 of FIG. 1, the measuring value is measured of the detector 23 along the path 91 in the position shown in FIG. 4. The correction value for the path 9 (FIG. 1), calculated by the interpolation and converted by the convolution process, is then replaced by the measuring value along the path 91 converted by the convolution process. However, because the path 91 generally does not coincide exactly with the path 9, interpolation must be effected by means of the two measuring values supplied by the detector 23 and converted by the convolution process, measured along two paths directly adjacent the path 9; this is effected in the interpolation unit 107.

As has already been stated, the measuring or correction values measured along neighbouring parallel paths are taken into account for the value of a path calculated by the convolution process. This means that the measuring values for paths directly adjacent the path for the correction value and extending parallel thereto, converted by the convolution process, are also influenced by errors during the measurement of the correction value. Therefore, these values would first have to be replaced in the same way as the correction value.

The described replacement of a correction value and the measuring values formed for neighbouring paths, by means of the convolution process, by measuring values which have been measured (in the reverse direction) along the path with which the correction value is associated or along directly adjacent paths by a detector which is symmetrically arranged with respect to the defective detector, relative to the symmetry line, or by the neighbouring detectors, said measuring values having been converted by the convolution process, is repeated for all measuring values of a defective detector. At the end of this processing phase, the memory 105 contains values which no longer substantially deviate from the values which would have resulted if no detectors were defective. The further completion of the calculation is effected in the same way as in known devices.

The foregoing description was based on the assumption that the detectors adjacent the defective detector are not defective. However, the invention also offers useful results if the directly adjacent detectors are also defective. In this case it is merely necessary to use further detectors or the measuring values thereof for the interpolation, and the interpolation formulas should then be changed accordingly.

What is claimed is:
1. A device for measuring the spatial distribution of radiation absorption in a slice of a body, said device comprising a radiator for generating a fan-shaped radiation beam for irradiating the body, a row of adjacently arranged radiation detectors for determining measuring values concerning the radiation emerging from the body, the measurements being performed in a number of different angular positions of the radiator/detector system with respect to the body, the direction of the radiation beam extending in the slice of the body, and also comprising a reconstruction device for determining the absorption distribution in the slice on the basis of the measuring values obtained, characterized in that the device comprises a testing device for identifying defective detectors, and also an interpolation unit for replacement of measuring values of a detector which has been identified as being defective by correction values, formed by interpolation of measuring values measured along paths adjacent the paths along which the measuring values have been measured by the defective detector.

2. A device as claimed in claim 1, wherein said device further comprises an interpolation unit for forming a correction value from measuring values measured by detectors situated adjacent the defective detector in the same position of the radiator/detector system as the measuring value of the defective detector to be replaced.

3. A device as claimed in claim 1, wherein said device further comprises an indicator which indicates the detectors which have been identified as being defective.

4. A device as claimed in claim 1, wherein said device further comprises an indicator which indicates the detectors which have been identified as being defective.

5. A device as claimed in claim 1, wherein said testing device for identifying defective detectors further comprises an arithmetic unit for determining the difference between the measuring values measured by each detector and the measuring value measured by at least one neighbouring detector, said arithmetic unit identifying a detector which exhibits a comparatively large measuring value difference with respect to the other detector in a large number of positions of the radiator/detector system as being defective.

6. A device as claimed in claim 5, wherein said arithmetic unit forms the sum of the measuring values of each detector, the sum values of the individual detectors thus obtained being subtracted from the sum values of at least one adjacent detector, the difference being assigned to the detector, the detectors where the magnitude of the difference exceeds a threshold value being identified as being defective.

7. A device as claimed in claim 1, in which the radiator/detector system is rotated through an angle of at least 360° during the measurements, the device further comprising means for performing a convolution process with the measuring values and correction values obtained, wherein said device includes an arithmetic device for substituting each correction value by a value which is formed from at least one measuring value measured along a path directly adjacent the path associated with the correction value.

8. A device as claimed in claim 7, wherein said device further comprises an interpolation unit for forming a correction value from measuring values measured by detectors situated adjacent the defective detector in the same position of the radiator/detector system as the measuring value of the defective detector to be replaced.

9. A device as claimed in claim 7, wherein said device further comprises an indicator which indicates the detectors which have been identified as being defective.

10. A device as claimed in claim 7, wherein said device further comprises an indicator which indicates the detectors which have been identified as being defective.

11. A device as claimed in claim 7, wherein said testing device for identifying defective detectors further comprises an arithmetic unit for determining the difference between the measuring values measured by each detector and the measuring value measured by at least one neighbouring detector, said arithmetic unit identifying a detector which exhibits a comparatively large measuring value difference with respect to the other detector in a large number of positions of the radiator/detector system as being defective.

12. A device as claimed in claim 11, wherein said arithmetic unit forms the sum of the measuring values of each detector, the sum values of the individual detectors thus obtained being subtracted from the sum values of at least one adjacent detector, the difference being assigned to the detector, the detectors where the magnitude of the difference exceeds a threshold value being identified as being defective.

13. A device as claimed in claim 7, wherein the measuring value, measured along a path by a defective detector and converted by a convolution process, and the measuring values, measured along the directly adjacent path and converted by the convolution process, are substituted by measuring values, converted by the convolution process and measured along the same paths, but in the opposite direction, of the detectors which are symmetrically arranged with respect to a defective detector and the adjacent detectors thereof.

14. A device as claimed in claim 13, wherein said device further comprises an interpolation unit for forming a correction value from measuring values measured by detectors situated adjacent the defective detector in the same position of the radiator/detector system as the measuring value of the defective detector to be replaced.

15. A device as claimed in claim 13, wherein said device further comprises an indicator which indicates the detectors which have been identified as being defective.

16. A device as claimed in claim 13, wherein said testing device for identifying defective detectors further comprises an arithmetic unit for determining the difference between the measuring values measured by each detector and the measuring value measured by at least one neighbouring detector, said arithmetic unit identifying a detector which exhibits a comparatively large measuring value difference with respect to the other detector in a large number of positions of the radiator/detector system as being defective.

17. A device as claimed in claim 16, wherein said arithmetic unit forms the sum of the measuring values of each detector, the sum values of the individual detectors thus obtained being subtracted from the sum values of at least one adjacent detector, the difference being assigned to the detector, the detectors where the magnitude of the difference exceeds a threshold value being identified as being defective.

18. A device as claimed in claim 1, in which the radiator/detector system is rotated through an angle of at least 360° during the measurements, the device further comprising means for performing a convolution process with the measuring values and correction values obtained, wherein said device includes an arithmetic device for substituting each correction value by a value which is formed from at least one measuring values measured by a detector which is symmetrically arranged with respect to the defective detector, relative to the symmetry line of the detector row.

19. A device as claimed in claim 18, wherein said device further comprises an interpolation unit for forming a correction value from measuring values measured by detectors situated adjacent the defective detector in the same position of the radiator/detector system as the measuring value of the defective detector to be replaced.

20. A device as claimed in claim 18, wherein said device further comprises an indicator which indicates the detectors which have been identified as being defective.

21. A device as claimed in claim 18, wherein said testing device for identifying defective detectors further comprises an arithmetic unit for determining the difference between the measuring values measured by each detector and the measuring value measured by at least one neighbouring detector, said arithmetic unit identifying a detector which exhibits a comparatively large measuring value difference with respect to the other detector in a large number of positions of the radiator/detector system as being defective.

22. A device as claimed in claim 21, wherein said arithmetic unit forms the sum of the measuring values of each detector, the sum values of the individual detectors thus obtained being subtracted from the sum values of at least one adjacent detector, the difference being assigned to the detector, the detectors where the magnitude of the difference exceeds a threshold value being identified as being defective.

23. A device as claimed in claim 18, wherein said measuring value, measured along a path by a defective detector and converted by a convolution process, and the measuring values, measured along the directly adjacent path and converted by the convolution process, are substituted by measuring values, converted by the convolution process and measured along the same paths, but in the opposite direction, of the detectors which are symmetrically arranged with respect to a defective detector and the adjacent detectors thereof.

24. A device as claimed in claim 23, wherein said device further comprises an interpolation unit for forming a correction value from measuring values measured by detectors situated adjacent the defective detector in the same position of the radiator/detector system as the measuring value of the defective detector to be replaced.

25. A device as claimed in claim 23, wherein said testing device for identifying defective detectors further comprises an arithmetic unit for determining the difference between the measuring values measured by each detector and the measuring value measured by at least one neighbouring detector, said arithmetic unit identifying a detector which exhibits a comparatively large measuring value difference with respect to the other detector in a large number of positions of the radiator/detector system as being defective.

26. A device as claimed in claim 25, wherein said arithmetic unit forms the sum of the measuring values of each detector, the sum values of the individual detectors thus obtained being subtracted from the sum values of at least one adjacent detector, the difference being assigned to the detector, the detectors where the magnitude of the difference exceeds a threshold value being identified as being defective.

27. A device as claimed in claim 1, in which the radiator/detector system is rotated through an angle of at least 360° during the measurements, the device comprising means for performing a convolution process with the measuring values and correction values obtained, wherein said device includes an arithmetic device for substituting each correction value by a value which is formed from at least one measuring values measured by neighbouring detectors thereof.

28. A device as claimed in claim 27, wherein said device further comprises an interpolation unit for forming a correction value from measuring values measured by detectors situated adjacent the defective detector in the same position of the radiator/detector system as the measuring value of the defective detector to be replaced.

29. A device as claimed in claim 27, wherein said device further comprises an indicator which indicates the detectors which have been identified as being defective.

30. A device as claimed in claim 27, wherein said testing device for identifying defective detectors further comprises an arithmetic unit for determining the difference between the measuring values measured by each detector and the measuring values measured by at least one neighbouring detector, said arithmetic unit identifying a detector which exhibits a comparatively large measuring value difference with respect to the other detector in a large number of positions of the radiator/detector system as being defective.

31. A device as claimed in claim 30, wherein said arithmetic unit forms the sum of the measuring values of each detector, the sum values of the individual detectors thus obtained being subtracted from the sum values of at least one adjacent detector, the difference being assigned to the detector, the detectors where the magnitude of the difference exceeds a threshold value being identified as being defective.

32. A device as claimed in claim 27, wherein said measuring value, measured along a path by a defective detector and converted by a convolution process, and the measuring vlaues, measured along the directly adjacent path and converted by the convolution process, are substituted by measuring values, converted by the convolution process and measured along the same paths, but in the opposite direction, of the detectors which are symmetrically arranged with respect to a defective detector and the adjacent detectors thereof.

33. A device as claimed in claim 32, wherein said device further comprises an interpolation unit for forming a correction value from measuring values measured by detectors situated adjacent the defective detector in the same position of the radiator/detector system as the measuring value of the defective detector to be replaced.

34. A device as claimed in claim 32, wherein said testing device for identifying defective detectors further comprises an arithmetic unit for determining the difference between the measuring values measured by each detector and the measuring values measured by at least one neighbouring detector, said arithmetic unit identifying a detector which exhibits a comparatively large measuring value difference with respect to the other detector in a large number of positions of the radiator/detector system as being defective.

35. A device as claimed in claim 34, wherein said arithmetic unit forms the sum of the measuring values of each detector, the sum values of the individual detectors thus obtained being subtracted from the sum values of at least one adjacent detector, the difference being assigned to the detector, the detectors where the magnitude of the difference exceeds a threshold value being identified as being defective.

* * * * *